United States Patent
Maurice

[11] 3,934,585
[45] Jan. 27, 1976

[54] METHOD AND APPARATUS FOR APPLICATION OF EYE DROPS

[76] Inventor: David M. Maurice, 148 Tuscaloosa Ave., Atherton, Calif. 94025

[22] Filed: Oct. 12, 1973

[21] Appl. No.: 405,786

Related U.S. Application Data

[63] Continuation-in-part of Ser. Nos. 63,363, Aug. 13, 1970, abandoned, and Ser. No. 114,133, Feb. 10, 1971, abandoned.

[52] U.S. Cl. ............... 128/225; 128/233; 222/420
[51] Int. Cl.² ............................................ A61M 3/00
[58] Field of Search .......... 128/225, 233, 234, 235, 128/173 H, 173 R, 230, 218, 215, 260, 249; 222/420–422, 386, 383, 394

[56] References Cited
UNITED STATES PATENTS

| | | | |
|---|---|---|---|
| 2,698,015 | 12/1954 | Brown | 128/233 |
| 2,704,543 | 3/1955 | Scherer | 128/173 H |
| 3,285,296 | 11/1966 | Ishimaru et al. | 128/233 X |
| 3,314,426 | 4/1967 | Carroll | 128/173 R |
| 3,506,001 | 4/1970 | Costello | 128/173 H |
| 3,512,524 | 5/1970 | Drewe | 128/233 X |

*Primary Examiner*—Robert W. Michell
*Assistant Examiner*—J. Yasko
*Attorney, Agent, or Firm*—Gregg, Hendricson, Caplan & Becker

[57] ABSTRACT

Method and apparatus for applying therapeutic eye drops to the eye by metering a predetermined volume of fluid and rapidly applying a pressure to one end of the metered fluid for forcing the fluid from a nozzle of means defining a small passageway such as an open-ended tube as a droplet having sufficient velocity to travel a generally horizontal distance in space to the eye. Unit dose application and multiple dose application are included and provision is made for preventing anticipatory blinking of the eye during self-administration.

14 Claims, 15 Drawing Figures

METHOD AND APPARATUS FOR APPLICATION OF EYE DROPS

This application is a continuation-in-part of prior application, Ser. No. 63,363 filed Aug. 13, 1970, now abandoned, and copending application Ser. No. 114,133 filed Feb. 10, 1971 now abandoned.

BACKGROUND OF INVENTION

Conventionally drops are applied to the eye with an eye dropper generally in the form of a glass tube having a rubber bulb at one end. This manner of application has a number of disadvantages such as discomfort from anticipation of the drop and involuntary blinking as the drop is seen falling into the eye, which may then result in the drop actually falling on the lids. Commonly an excess of fluid in the drop runs onto the skin about the eye and this is not only inconvenient but also gives rise to the possibility of systemic poisoning by absorption of particular fluids through the skin. Furthermore, and particularly applicable to self-administration of eye drops, is the problem of uncertain dosage originally applied and the indeterminate fraction thereof that is squeezed out of the eye by reflex blinking.

Aside from the occasional administration of eye drops as may occur with many people, there is also the necessity of continued use of eye drops in certain instances. Thus, for example, in the treatment of glaucoma it is conventional to prescribe four drops of pilocarpine per day for life. The necessity of continued usage of eye drops as in the foregoing instance usually requires the drops to be self-administered and the present invention is particularly adapted to this application.

SUMMARY OF INVENTION

The present invention provides for the metering or measurement of a predetermined small amount of volume of liquid or the like in a small open-ended tube. The liquid in the aforementioned tube is instilled or projected into the eye by the sudden application of a force or pressure to the liquid in the tube for ejecting such liquid from the open tube end with sufficient velocity to travel through space into the eye of the subject. The metering of the liquid may be accomplished in a variety of ways including the provision of a metered dose into an open-ended tube which is adapted to be employed for unit dose application. Alternatively the invention provides for the application of successive metered doses from a reservoir or container adapted to hold a multiplicity of doses of liquid. Furthermore, the present invention provides alternatives in the manner of suddenly applying pressure to the predetermined volume of liquid in the above-noted open-ended tube. For example, there may be employed a "puff" of air which has been previously compressed and is then subsequently applied to the liquid at one end of the open-ended tube for ejection of the liquid from the other end as a small drop or droplet with only sufficient velocity to travel through space into the eye of the subject. Alternatively, the present invention provides for the sudden release or application of pressure to a piston or the like engaging a liquid in an open-ended tube or the like for the forcible ejection of the liquid therefrom.

In accordance with the present invention a small volume of liquid of about 10 cubic millimeters or 10 microliters is injected into the eye or, more properly, is applied to the surface of the eye so that virtually all of the liquid is retained in the eye even though the patient may blink after application of the liquid and, furthermore, the force of application is sufficiently small that there is little sensation of liquid instillation in the eye. Provision may also be made in accordance with the present invention for properly directing the liquid into the eye as, for example, by means of a small mirror that may be mounted upon the injector, or other suitable aligning means being provided with the injector. Alternatively, the present invention provides for automatic aligning of the injector hereof with the eye by the means of an "eyecup" which is adapted to be pressed against the eyelids to hold same open and to automatically direct the above-noted open-ended tube into the eye so that even involuntary blinking cannot prevent application of the liquid. As noted above, the present invention is particularly adapted to unit dose application wherein a preloaded tube or the like contains the desired volume of liquid for a single injection and such tube is adapted to be utilized with the injector of the invention to forcibly inject such predetermined volume of liquid into the eye. This application is normally termed a unit dose application. In addition the present invention is also adapted to the injection of a predetermined volume of liquid into the eye as a small drop or the like traveling in space from a container having a substantial volume of liquid therein for multiple dose application. A wide variety of different liquids are employed as eye drops for various medicinal purposes and the present invention is applicable for use with any such liquid.

DESCRIPTION OF FIGURES

The present invention is illustrated both as to method and apparatus thereof in the accompanying drawings wherein.

DESCRIPTION OF PREFERRED EMBODIMENTS

The method of the present invention briefly comprises the substantial filling of a very small open-ended tube or means defining a small passageway with a liquid to thus establish or meter a desired dosage or drop of desired volume. This tube is then directed with an open or nozzle end thereof toward the eye to be injected with the liquid in the tube and is spaced a short distance form the eye. The present invention then proceeds to rapidly apply a substantial pressure to the liquid in the open-ended tube to thus force the liquid from the tube nozzle as a small drop or droplets, with sufficient velocity to travel through space into the eye at which the nozzle or open-ended tube is directed. The aforementioned pressure may be applied as a rapid application of compressed air in the form of a "puff of air", or, alternatively, may be applied by the sudden release of a restrained resilient member as through a piston such that the piston then moves at least in substantial part through the passageway to force the liquid from the open end or nozzle thereof.

A small volume of liquid is injected in accordance with the present invention and preferably this volume is less than about 10 microliters. It has been determined that the volume of lacrimal fluid normally in the eye is about 10 microliters and that this added volume of liquid produces adequate concentrations without overflow. It is furthermore noted that the amount of compressed air or puff of air that is employed to inject the liquid is preferably less than 200 microliters at an excess pressure of some small fraction of an atmosphere so that there will be produced very little, if any, sensation upon instillation. The liquid should be ejected from the nozzle or the like at sufficient velocity to travel into the eye without undue spreading but with insufficient velocity to cause discomfort or injury to the eye, as further noted below. It is also noted that the method of the present invention may be carried out with the head of the patient upright to thus add to the convenience of the method.

Figure 1:
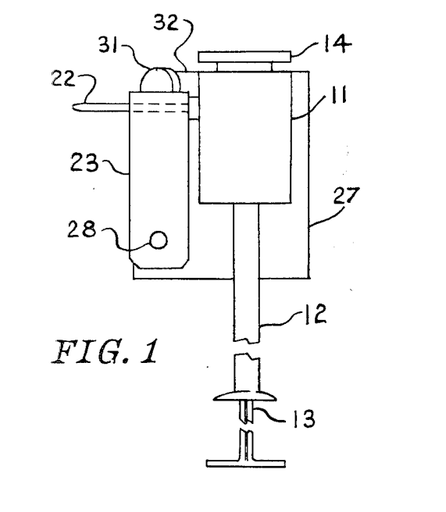
FIG. 1 is a side elevational view of a preferred embodiment of the injector of the present invention.
Figure 2:
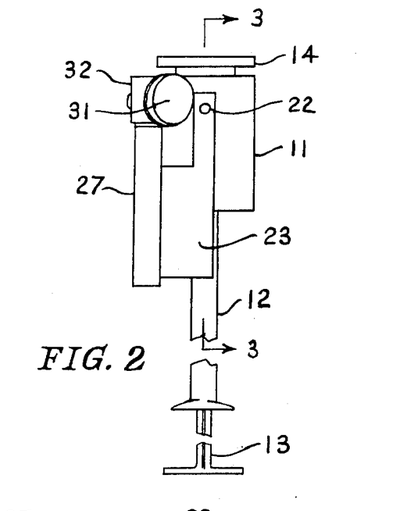
FIG. 2 is a front elevational view of the injector of FIG. 1.
Figure 3:
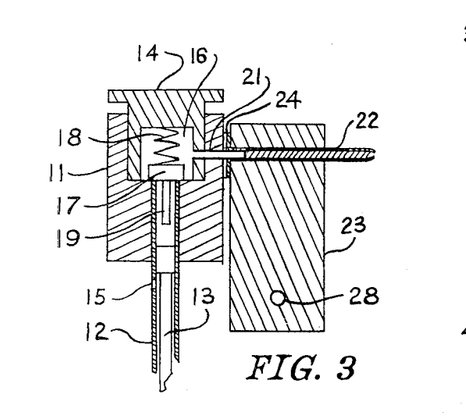
FIG. 3 is a sectional view taken in the plane 3—3 of FIG. 2.

Considering now a preferred embodiment of the invention, and referring to FIGS. 1 to 3, there is shown an injector body 11 having a depending hollow cylinder 12 within which is fitted a plunger 13 extending from the bottom open end of the cylinder. A hollow insert 14 is fitted into the top of body 11 to thus define a small chamber 16 within the body. A normally closed valve is formed between the inner end of the cylinder 12 and the chamber 16 by the provision of a small plate or the like 17 disposed across the end of the cylinder 12 and normally maintained in this position by a compression spring 18 disposed above same. An actuator pin 19 may be provided in extension below the plate 17 into the cylinder 12 so as to be mechanically engaged by the plunger 13 as it is moved upward in the cylinder. A side aperture 15 is provided in the cylinder 12 to admit air above the plunger 13 and the location of this opening sets the volume of air compressed above the plunger.

The injector as briefly described above also includes a very small tube 21 extending laterally through the housing 11 and slightly outward from a face thereof. Provision is made for removably connecting a dispensing tube 22 to the housing tube 21 as, for example, by means of a pivot block 23. The block 23 has a small aperture therethrough within which the dispensing tube 22 is adapted to fit and the dispensing tube 22 may have a flange 24 about the rear end thereof to fit against the face of the pivot block when the dispensing tube is inserted in the aperture therein. A plate 27 is mounted on the side of the injector housing 11 and the pivot block 23 is pivotally mounted upon this plate by means of a bar or axle 28.

There is additionally provided as a portion of the present invention means for properly directing the dispensing tube 22 toward the eye of a user, particularly during self-administration of an eye drop. Such means may simply comprise a concave mirror 31 mounted as by means of a bracket 32 upon the side plate 27. The mirror 31 is properly oriented with respect to the direction of extension of the dispensing tube 22 from the injector such that when the injector is placed about an inch away from the eye and the patient focuses the pupil of his eye in the center of the mirror, the dispensing tube is directed toward the exposed portion of the eyeball so that operation of the invention will thus cause the liquid to be injected into the eye.

Although the dispensing tube 22 may take a variety of different shapes and may be formed of a variety of materials such as a suitable plastic, for example, it is noted to be generally illustrated in FIG. 3 as comprising a thin elongated hollow tube open at both ends and having a flange about one end. In practice it has been found that a tube having a length of the order of 1 inch is appropriate and furthermore that the internal volume of the tube should be about 5 microliters per cm. Various alternative configurations of the dispensing tube are possible as described below in connection with FIGS. 4 to 6; however, in practice it has been found that with a tube of the size indicated almost any open-ended tube configuration is appropriate.

The dispensing tube 22 is preferably formed with a nozzle end as illustrated in FIG. 3, for example, and in fact such end may actually be formed as a section of reducing diameter toward the outer end thereof. Furthermore it is noted that the limited diameter of the tube provides for retention of fluid therein by capillary action and for attaining a desired fluid velocity therefrom, taking into account the desired volume of fluid to be ejected.

Considering now operation of the present invention as described above, the dispensing tube 22 is first filled preferably at a factory or the like and sold in filled form. This point is taken up further below. With the dispensing tube 22 filled with a liquid, such tube is then inserted into the aperture in the pivot block 23 from the rear of the block. This is readily accomplished by pivoting the block away from the injector housing and inserting the dispensing tube into the block. The tube fits the block snugly and is inserted until the flange 24 in the rear of the tube engages the rear face of the pivot block. The block is then pivoted upwardly toward the injector housing 11 so that the small housing tube 21 enters the rear end of the dispensing tube as illustrated in FIG. 3. The injector is then in condition for use. In order to apply a small drop or droplet of liquid such as pilocarpine, as used for glaucoma, into the eye, the overall unit is placed directly in front of the eye to be injected. The user or patient looks into the mirror 31 and moves the injector to a point at which the eye is directly in focus in the mirror as viewed by the patient and the pupil of the eye is reflected in the center of the mirror. As noted above, this will place the injector about an inch or less from the eye with the dispensing tube 22 pointed toward the eye, possibly somewhat off center thereof. The plunger 13 is then pressed into the cylinder 12. This causes air at the top of the cylinder 12 to be compressed and in the illustrated embodiment this plunger then engages the pin 19 depending from the valve plate 17 and raises the valve against the pressure of spring 18. Consequently a puff of compressed air is applied through the chamber 16 and the housing tube 21 into the rear end of the dispensing tube 22. A liquid within the tube is thus forcibly ejected form the open front end of the tube as a small drop with sufficient velocity that is travels through the atmosphere into the eye. As noted above, the volume or liquid injected is quite small, as of the order 10 mm$^3$ and furthermore the amount of air employed in injecting this small drop or droplet is maintained small, as of the order of 200 mm$^3$, so that very little sensation results from the injection. Furthermore with this small amount of liquid being injected, even though the patient blinks his eye after receipt of the dosage, the injected liquid remains in the eye.

Figure 4:
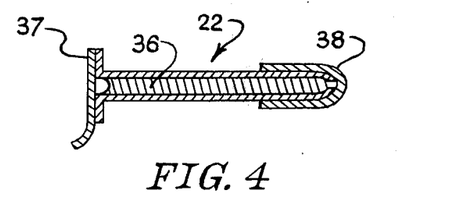
FIGS. 4, 5 and 6 are illustrations of different configurations of dispensers as may be employed to hold and sterilely retain a unit dose of liquid.
Figure 5:
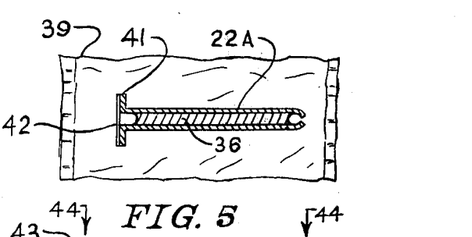
Figure 6:
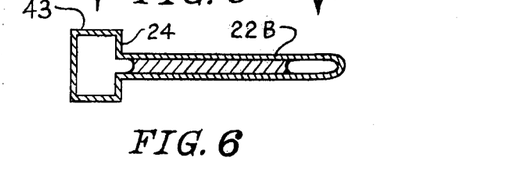

Various modifications and alternatives are possible within the scope of the present invention. In particular it is noted that the present application is particularly adapted to unit dose application. There has been an increasing emphasis upon the sterility of medicines and their containers and predetermination of doses of medicines to be administered to patients both for self-administration and also for use in doctors' offices, hospitals, and the like. The present invention is particularly adapted to this unit dose approach inasmuch as the dispensing tube 22 is formed of such a size that it will only contain a known small amount of liquid. The tube may be filled with the proper liquid prior to dispensation either to professional personnel for utilization or to patients for self-administration. Referring to FIGS. 4, 5 and 6, there will be seen to be shown various possibilities in connection with unit dose application of the present invention. FIG. 4 illustrates the dispensing tube 22 as being filled with a liquid 36 and having both tube ends sealed. The flanged end of the tube may be sealed by an adhesive strip 37 adhering to the flange and extending slightly therefrom so that it may be readily gripped and stripped from the flanged end of the tube. The opposite end of the tube may be closed as, for example, by a small plastic cap 38 which slips over the end of the tube and firmly grips it. With this structure the tube may be filled with liquid and then sealed for handling and dispensing while at all times maintaining the tube ends sterile and also ensuring that the liquid remains within the tube and furthermore it does not evaporate therefrom. It is to be appreciated that the illustrations of dispensing tubes in FIGS. 4 to 6 are only schematic for, in fact, the total tube length may be of the order of one inch and the tube diameter of the order of 1/64th of an inch. Furthermore the illustrations in these Figures are taken as central section views for the purpose of showing the different structures and sealing means.

There is illustrated in FIG. 5 a dispensing tube 22A containing a liquid 36 and sealed within a plastic envelope schematically illustrated at 39. This particular tube 22A may, for example, have a flanged rear end as shown at 41 and include a thin membrane 42 secured across the flanged end. The fron end of the dispensing tube need not be tapered as illustrated in other Figures of the drawings but may, in fact, be merely a cutoff end of the tube or, alternatively, may have the tube edges turned inwardly somewhat as illustrated in FIG. 5. With the envelope sealed the tube and contents are fully protected for handling and shipping and with regard to the rear membrane 42 same is discussed in more detail below in connection with utilization of same.

In FIG. 6 there is illustrated a dispensing tube 22B having the front end thereof sealed as by tube closure and again containing an apropriate liquid 36. The rear end of the tube is formed as an expanded portion having the tube flange 24 as one wall thereof and the remaining walls closing the end of the tube as indicated. The physical shape of the expanded portion 43 of the tube 22B is not of major importance but it is noted that same should have a sufficient length longitudinally of the tube that this portion may be sliced or cut to thus open the rear tube end. Similarly the front closed portion of the tube is adapted to be cut and such cuts are indicated by the arrows 44 in FIG. 6. In this instance the dispensing tube may, for example, be formed of plastic and furthermore provision may be made in the injector itself or apparatus to be used therewith for cutting the tube ends. Insofar as filling and sealing of the tube is concerned, it is appreciated that a variety of different techniques are possible and, for example, the sealed ends may be formed after the tube is filled. This particular embodiment of the invention is probably best suited to utilization at a manufacturing plant wherein the tubes are formed, filled sealed and shipped. It is to be noted that, in all instances whatever the physical configuration of the individual dispensing tube, it is possible to encase same in a sterile container such as the envelope 39 of FIG. 5. It is not intended by the illustration of FIGS. 4 to 6 to limit the present invention to the particular tube embodiment shown therein but, instead, these illustrations and the foregoing description thereof are intended primarily for the purpose of indicating variations without limitation.

Figure 7:
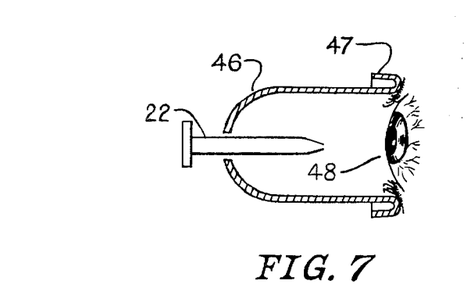
FIG. 7 is an illustration of dispenser and eyecup as may be employed with an injector such as shown in FIGS. 1 and 2.

In FIG. 7 there is illustrated an alternative embodiment or addition that may be employed with the present invention particularly for use in self-application of eye drops. In FIG. 7 there is not illustrated the injector structure but instead the Figure shows only the dispensing tube 22 which is understood to be mounted as in FIG. 1 but to extend into an open-ended housing 46 having somewhat the form of an eyecup adapted to fit into the orbital margin of the eye. The tube extends generally axially through the bottom of the cup 46 which in turn may be suitably mounted upon an injector housing. The outer ends of the cup 47 may be curved or thickened as indicated. As will be seen from the illustration of FIG. 7, the eyecup 47 is adapted to be pressed against the lids of an eye 48 to be injected with the invention. With the cup disposed as shown, the eyelids are thus held open and, furthermore, the dispensing tube is properly directed toward the eye so that upon actuation of an injector in which the dispensing tube is mounted, the small drop or droplet of liquid will be directly injected into the eye. By holding the eyecup in this position during use, involuntary blinking is impeded. This particular embodiment of the invention is also useful for those that may have difficulty seeing, as the physical feeling of the eyecup located about the eye with the eyelids pulled apart ensures the user that the dispensing tube is properly directed to inject a drop into the eye.

Figures 8, 9, 10:
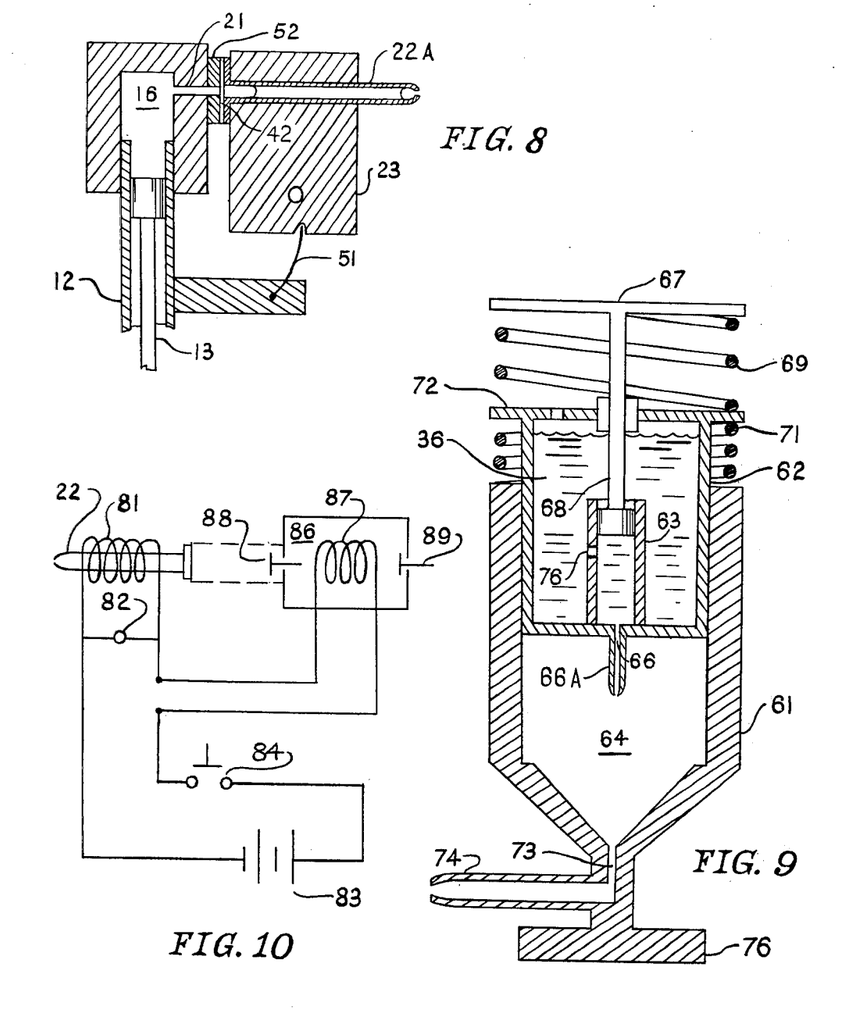
FIG. 8 is a partial illustration of injector mounting of a dispenser such as illustrated in FIG. 5.
FIG. 9 is a longitudinal sectional view of an alternative embodiment of an injector in accordance with the present invention and adapted to inject repeated dosages of liquid.
FIG. 10 is a schematic wiring diagram of an alternative embodiment of the present invention.

There is illustrated in FIG. 8 a portion of a simplified injector utilizing a dispensing tube 22A such as illustrated in FIG. 5. In this instance the tube 22A is shown to be mounted in a pivot block 23 that in this instance is spring loaded as by a leaf spring 51 to urge the block and thus the tube against the injector housing 11. Within the housing 11 there is formed a small chamber 16 having a tube 21 extending laterally therefrom for engagement with the membrane 42 across the rear end of the dispensing tube. A gasket 52 may be provided about the outer end of this housing tube 21 so that the membrane then rests tightly against this gasket, or the tube flange may merely fit tightly against the housing to form a seal. Such contact is maintained by the spring 51 and, of course, such a spring may be used in the embodiment of FIGS. 1 to 3 instead of the tube engagement. The cylinder 12 extends from the housing chamber 16 with the plunger 13 in the cylinder. In the position illustrated in FIG. 8 it is only necessary for the plunger to be forced upwardly in the cylinder to thus compress air in the chamber 16 to a point wherein the pressure is great enough to burst the membrane 42. This then allows the compressed air to forcibly eject the liquid 36 from the outer end of the dispensing tube 22A. It will be seen that, by the utilization of a particular membrane 42 across the rear end of the dispensing tube, it is possible to eliminate the valving and spring loading in the injector housing. The membrane takes the place of these elements. However, it is to be appricated that the membrane is to be made of a material having known properties and with a prdetermined thickness of material so that in each case the same maount of pressure on the limited area thereof to which it is applied will, in fact, burst the membrane. Thus, this embodiment of the present invention has the dual advantage of providing a seal across one end of the dispensing tube and also of simplifying the injector mechanism.

Various modifications of the present invention are possible to provide for multiple injections, and as an example thereof an alternative embodiment of the present invention is illustrated in FIG. 9 of the drawings. Referring thereto it will be seen that there is provided a housing 61 having an open end within which there is slidably disposed a hollow piston 62. This piston 62 is closed and is adapted to contain a liquid 36 for injection as small predetermined drops into the eye of a patient. Within the piston 62 there is provided an upright hollow cylinder 63 extending axially of the piston and communicating with a chamber 64 in the housing through a very small opening 66 in the bottom of the piston. A nozzle 66A is preferably provided in extension downwardly from the opening 66. Such nozzle is provided to ensure that liquid ejected from the interior of cylinder 63 does in face emerge as a droplet to fall to the bottom of chamber 64. A plunger 67 extends through the top of the piston with the shaft 68 thereof fitting into the hollow cylinder 63. A compression spring 69 is disposed between the top or handle portion of the plunger 67 and the top of the piston 62 in order to normally urge the plunger out of the piston. There may also be provided a compression spring 71 between the top of the housing 61 and a flange 72 about the top of the piston so as to also urge the piston into an upwardly disposed such as illustrated in FIG. 9. Note also that the device of FIG. 9 must be employed in the upright position, as illustrated.

The chamber 64 in the housing 61 beneath the piston 62 has a tapered lower end as illustrated with a very fine tube or opening 73 at the bottom thereof leading to a laterally extending dispensing tube 74. A flat projection 76 may be provided at the bottom of the housing to assist in gripping the unit during use.

With regard to operation of this particular embodiment of the present invention, it is first noted that the opening 66 is made much smaller than the opening 73 and furthermore that the distance between the top of the piston 62 and the plunger handle 67 is made substantially equal to the distance between the bottom of the plunger shaft 68 and the bottom of the piston 62. With a liquid in the piston 62 and the unit in the position illustrated, the unit is gripped as, for example, by placing the fingers on the plunger handle 67 and the thumb beneath the bottom projection 76. The plunger is then depressed, which will be seen to force fluid through the small opening 66 into the housing chamber 64. It is noted that a side opening 76 is provided in the cylinder 63 within the piston in order that fluid may flow from the interior of the piston into the inside of the cylinder below the plunger shaft so as to normally fill the cylinder. With the plunger depressed so that the top thereof engages the top of the piston or substantially engages it with the spring 69 compressed therebetween, further downward movement of the plunger will cause the piston to be moved downward against the pressure of the compression spring 71. This will then compress air within the chamber 64.

Considering further the operation of the embodiment illustrated in FIG. 9, it is noted that liquid 36 is first forced into chamber 64 by initial downward movement of the plunger 67. This liquid forms a small pool at the bottom of the chamber 64 atop the fine opening or tube 73 and is slowly forced therethrough into the dispensing tube 74 by air pressure as the piston 62 is forced downward in the chamber 64 by the plunger 67. The volume of liquid forced from the cylinder 63 is substantially equal to the volume of liquid to be dispensed by the device. As all of the liquid passes from the passage 73 into the tube 74 the compressed air in the chamber 64 then acts on the liquid at the inner end of the tube 74 to forcibly eject liquid from the outer tube end in the manner of a valve action. The liquid is thus forcibly ejected from the outer end of the dispenser tube 74 as a small drop or droplet. The viscosity of the liquid 36 may be varied to control or adjust the valve action of this device.

After administration or injection of a drop of liquid, the plunger is released and subsequently the spring 71 moves the piston back up to the position illustrated in FIG. 9 and the spring 69 moves the plunger upwardly to the position illustrated. As the plunger moves upwardly the bottom thereof passes the small opening 76 in the side of the cylinder 63 in the piston so that liquid again flows into the cylinder below the bottom of the plunger shaft. The unit is then ready for further use to inject another drop. It will be seen that this embodiment of the present invention provides a reservoir within the unit so the drops may be repeatedly applied from the unit.

It is noted that in the application of drops to the eye one of the unpleasant sensations encountered is the coldness of the drop itself. This sensation may be overcome by warming the drop. The embodiment of the present invention illustrated in FIG. 10 not only accomplishes this result but furthermore provides for an alternative manner of providing compressed air for drop injection and at the same time provides a time delay following actuation so that the patient will not involuntary blink upon anticipation of a drop being inserted in the eye. In FIG. 10 there is provided a schematic illustration of an injector in accordance with the present invention and having the above-noted capabilities. A suitably supported dispensing tube 22 is shown to be disposed within a heating coil 81. A thermistor 82 may be connected across the coil to ensure that the tube and consequently the liquid therein is always heated to approximately the same temperature regardless of ambient temperature. The heating coil 81 is connected across a bettery 83 by means of a switch 84. In addition there is provided in this embodiment of the present invention a small air chamber 86 having heating coil 87 therein or thereabout, with such coil being also connected across the battery 83 by means of the switch 84. A spring loaded outlet valve 88 connects the chamber 86 with the rear end of the dispensing tube 22.

It will be seen that, upon closure of the switch 84, current is supplied to the two heating coils 81 and 87 so as to thus heat the liquid in the dispensing tube and also to heat the air in the chamber 86. As the air in the chamber 86 reaches a sufficient temperature the pressure thereof will rise to the point wherein it will open the valve 88 and thus the heated and consequently compressed air in the chamber will be applied to the tube 22 for forcing the warm liquid from the end thereof. By choice of appropriate element parameters the temperature of the liquid will at no time be heated above that of normal body temperature and it will be appreciated that it is well within the skill of those knowledgeable in the art to properly proportion the heating between the chamber and tube so that the compressed air is applied as a puff to the rear end of the dispensing tube at the time that the liquid in the tube reaches the desired temperature. There may also be provided a spring loaded inlet valve 89 for the chamber 86 in order that air may be re-admitted thereto after it has been heated, compressed and expelled.

It has been noted above that the present invention provides for metering of liquid to obtain a desired volume thereof for injection into the eye and, furthermore, provides for the sudden application of a force to one end of this metered amount of liquid contained in an open-ended injector so that the metered amount of liquid is thus ejected therefrom. In the embodiments of the present invention described above, there are set forth certain alternatives in the manner of metering the liquid. Each of the foregoing embodiments of the present invention has, however, employed a puff of gas, such as compressed air, to apply the ejection force for the metered liquid.

Figures 11, 12, 13, 14, 15:
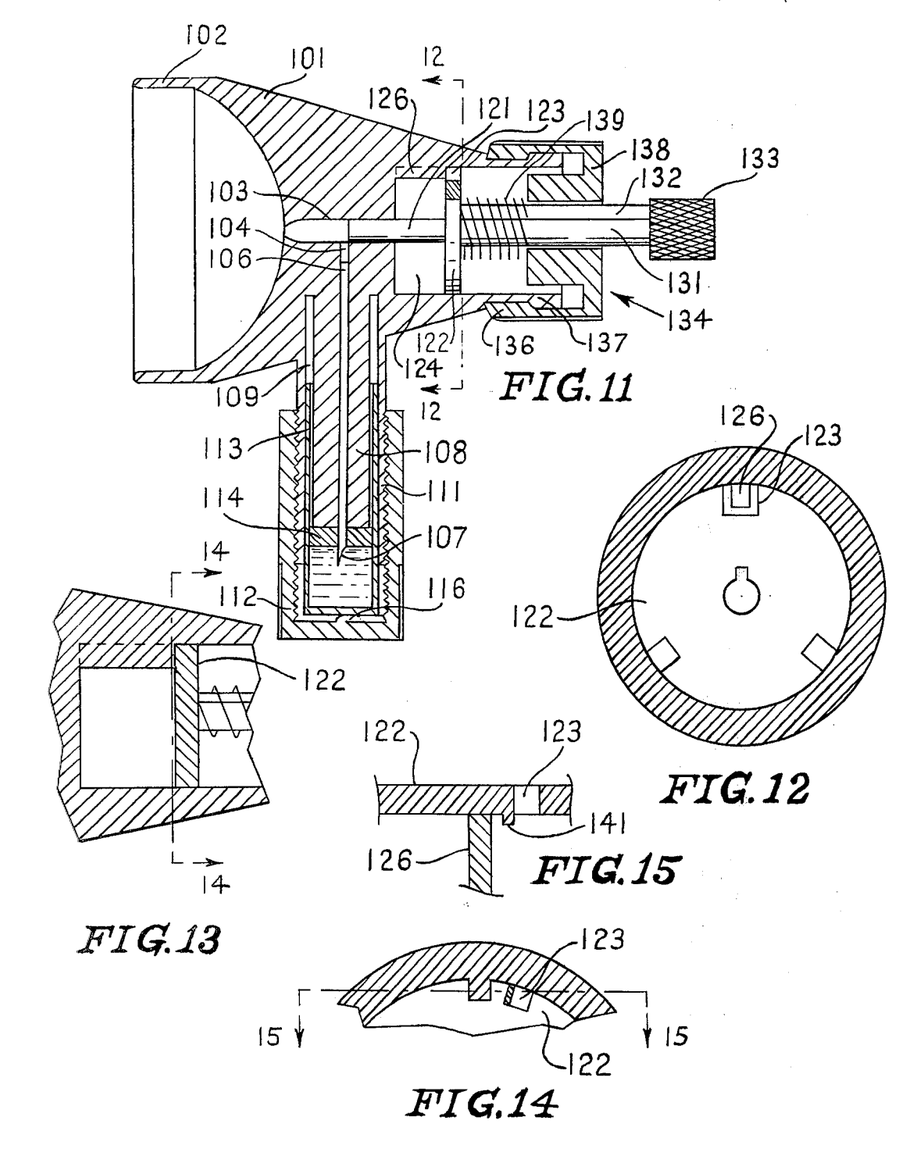
FIG. 11 is a central sectional view of another embodiment of the present invention adapted for multiple dose application.
FIG 12 is a sectional view taken in the plane 12—12 of FIG. 11.
FIG. 13 is a partial sectional view of alternative release mechanism for an injector such as shown in FIG. 11.
FIG. 14 is a partial sectional view taken in the plane 14—14 of FIG. 13.
FIG. 15 is a partial sectional view taken in the plane 15—15 of FIG. 14.

In FIg. 11 there is illustrated a further embodiment of the present invention incorporating multiple dose application and alternative force application for dose ejection. It will be appreciated that the embodiment of FIG. 11 may also be employed for unit dose application.

Referring now to FIG. 11 it will be seen that the applicator thereof includes a body 101 which may, for example, be formed of plastic or the like and provided at its forward end with an eyecup 102 having a size such as to completely surround the eye of the user of the applicator. An axial passage 103 extends through the body into communication with the inner end of the eye cup 102 to form the nozzle of the apparatus. A transverse passage 104 connects with the axial passage 103 and a hollow needle 106 fits within this transverse passage with a pointed end 107 extending from the passage. The body 101 includes a depending projection 108 through which the transverse passage 104 extends and a deep annular groove 109 is disposed about the aperture 104 with a cylindrical extension 111 about this groove. The cylindrical extension 111 about the projection 108 has the lower external portion thereof threaded to receive an internally threaded cylindrical cap 112. A capsule 113 adapted to contain eye drop fluid has a cylindrical configuration dimensioned to fit within the annular groove or slot 109 and a self-sealing plug or the like 114 slidably engages the capsule at the top thereof. The interior of the cap 112 may be provided with a small boss 116 on the inner side of the end of the cap for engaging the lower end of the capsule 113.

In use the capsule 113 is placed on the end of the projection 108 and urged upwardly with the walls of the capsule fitting into the annular slot or groove 109 so as to force the sharpened point 107 of the needle 106 through the top sealing member 114 of the capsule. The cap 112 is then threaded upon the threaded cylinder 111 so that the capsule plug 114 bears upon the lower end of the projection 108 and turning of the cap 112 will force the capsule up about the projection 108 to thus force eye drops or other fluid in the capsule through the needle into the axial passage 103 of the body 101.

Eye drops are forcibly ejected from the embodiment of the present invention illustrated in FIG. 11 by means of a plunger 121 slidably fitted into the axial passage 103 and carrying a disc 122 having at least one peripheral slot 123 therein. This disc 122 is disposed in a chamber 124 communicating with the back of the axial passsage 103 and an axial spline or the like 126 on a wall of the chamber 124 is dimensioned to fit through the slot 123 in the disc so that rotation of the disc will cause one of the slots 123 thereof to become aligned with the spline so that the plunger 121 may be moved to the left in the axial passage 103. The plunger 121 is extended through the disc 122 by a rod 131 having a spline 132 extending longitudinally thereof. The rod terminates in a knob 133 which may be knurled or the like, as indicated, for ready gripping. The rear of the chamber 124 is closed by a cap 134 or sleeve which has an internal flange 136 about the inner end thereof mating with an annular depression about an annular wall 137 defining the rear of the chamber. The cap 134 has a rear wall 138 through which the rod 131 and spline 132 extend in slidable relation thereto.

There is provided within the chamber 124 a compression spring 139 disposed about the rod and spline between the disc 122 and end wall 138 of the cap 134. This spring urges the disc and thus the plunger 103 to the left in FIG. 11. It will be appreciated that the cap 134 is apertured to receive the rod and spline in extension therethrough; however, the aperature is formed so that rotation of the cap upon the wall 137 will rotate the rod because of the spline engagement with the cap. This then provides for rotating the disc 122 so that the slot 123 in the disc will at some indeterminate point align with the axial spline 126 so that the spring 139 will force the plunger 121 through the axial passage 103.

In operation of the embodiment of the present invention illustrated in FIG. 11, an ampule or capsule of material to be ejected by the invention is attached to the body in the manner described above so that the needle extends into the fluid. The lower cap 112 is then rotated to force fluid upwardly into the axial passage 103. Filling of the axial passage is determined by noting overflow of the fluid into the eyecup. Alternatively, graduations may be provided upon the cylindrical extension 111 so that a predetermined amount of fluid may be forced into the axial passage by rotation of the cap. Prior to filling of the axial passage 103 the plunger 121 is retracted by gripping the knob 133 and drawing the piston and disc to the right in FIG. 11. Withdrawing of the plunger compresses the spring 139 and when the plunger is retracted the knob is then slightly turned so that the slot or slots in the periphery of the disc do not align with the axial spline 126. Consequently the spline then prevents the plunger from moving to the left in FIG. 11 and the device is cocked for use. After the eye drop material is disposed in the axial passage 103, a user places the eyecup 102 over the eye to be injected and rotates the cap 134 at the rear of the body 101. Rotation of this cap turns the disc 122 and at sometime during this turning a peripheral slot 123 in the disc aligns with the axial spline 126 so that the plunger is rapidly forced to the left in FIG. 11 by the compression spring 139. This then applies the force to the fluid to eject it from the axial passage 103. It is particularly noted that ejection of fluid occurs at an indeterminate time inasmuch as the user is slowly rotating the cap 134 and will thus not realize at what instant the disc will be freed so that the plunger moves to the left and consequently the user does not blink his eye in anticipation of eye drop injection.

In FIG. 12 there is illustrated a sectional view taken in the plane 12—12 of FIG. 11 and showing a disc 122 having a plurality of circumferentially spaced peripheral slots 123 therein. This disc configuration is substantially the same as described above and the illustration serves to show possible location of a plurality of release points by the spaced slots 123. An alternative arrangement for fluid ejection from the present invention without anticipation by the user so that he will blink his eye and defeat the process is illustrated in FIGS. 13 to 15.

Referring now to FIGS. 13 to 15, it will be seen that the disc 122 is provided with a small flange or protuberance 141 along one side of a single peripheral groove or slot 123 in the disc. This flange or the like 141 then prevents the disc from being rotated in one direction when it is forced against the spline 126 by the spring 139. Consequently when the device is cocked by drawing the knob 133 out of the body of the device, the user withdraws the disc far enough so that he can slightly turn the knob to pass the disc flange 141 over the axial spline 126 to place the elements in the relationship best shown in FIG. 15. Subsequent use of the device to eject an eye drop or the like is then accomplished by rotating the cap or sleeve 134, as described above; however, in this instance, substantially 360° of rotation are required and the user thus loses track of the location of the disc slot relative to the axial spline and consequently does not anticipate the instant of eye drop release or ejection by the device. This then provides another manner of preventing the user from blinking immediately prior to eye drop injection. It will be appreciated that various other modifications and variations are possible to the end of ejecting an eye drop either at an indeterminate time or position of elements in order to preclude the prevalent problem of a user blinking immediately prior to eye drop injection. Reflex actions of the user are thus prevented from interfering with eye drop injection.

It will be appreciated that the slower the velocity of the drop on striking the eye the less will be the discomfort associated with its injection. It is preferable therefore that the spring pressure or other fluid ejection force be such that the drops leave the injector with as low a velocity as possible consistent with a trajectory ensuring its entry into the eye. A drop ejected horizontally about 1 cm from the eye with a velocity of 50 cm/sec. would fall about 2 mm in its trajectory and should hit the eye above the lower lid. This velocity is similar to that attained by a drop falling about 1 cm vertically under the force of gravity.

There has been described above various emdobiments of the present invention directed to the forcible ejection of a small drop of fluid for injection of same into the eye. It is not intended herein that the invention shall eject a disperse fog or mist, for the results of same would be to spread the fluid over the face or lids of the user rather than directing it into the eye where it is intended to be deposited. In order to ensure small drop ejection from the present invention, it is preferable to form the nozzle diameter with a dimension in excess of 0.011 inch and a preferred nozzle diameter lies in the range of 0.02 inch to 0.04 inch. With this nozzle diameter and preferred volume of fluid, the present invention then ejects a single small drop of fluid and injects this drop between the lids of an eye at a relatively low velocity, as discussed above, rather than ejecting a spray which spreads over the entire area of the eye. It has been found that drop injection as described herein is highly advantageous and a preferable manner of applying medicaments to the eye.

There has been described above an improved method and apparatus for the injection of liquid into the eye. A number of different embodiments of the apparatus of the present invention have been illustrated and described. It is not, however, intended to limit the present invention to the details of illustration or description, as the alternative embodiments are set forth as exemplary rather than limiting. Reference is made to the following claims for a definition of the invention.

What is claimed is:

1. An eye drop dispenser comprising:
   housing means defining a small passageway terminating in a nozzle and adapted to contain an eye drop liquid to be dispensed,
   means engaging said housing means for directing said nozzle toward an eye to be injected,
   a plunger slideably mounted in said housing for movement into the said passageway,
   a spring engaging said housing and plunger for urging said plunger into said passageway under spring pressure, and
   controllable release means for restraining said plunger from moving into said passageway rotatably mounting said plunger relative to said housing and including visually obstructed engaging surfaces of said plunger and housing with each of said surfaces having at least one abruptly varying contour about said plunger and means for rotating said plunger to release said plunger at least once each revolution thereof to rapidly move under spring pressure into said passageway for forcibly ejecting liquid from the open end of said passageway at an indeterminate point of operation of the release means whereby a user does not blink at eye drop injection.

2. The dispenser of claim 1 further defined by:
   said release means including a notched disc about said plunger and urged by said spring against a spline in said housing means whereby rotation of said plunger and disc aligns a disc notch with said spline to release the plunger from movement to force said liquid from said passageway.

3. The dispenser of claim 1 further defined by said nozzle having a diameter in the range of 0.02 inch to 0.04 inch whereby liquid is ejected as a drop from the dispenser.

4. A multiple dose eye drop dispenser comprising
a body having a bore extending therein from an open end,
a cylinder adapted to carry a container of eye drop liquid and having an open end,
means extending from said body for engaging said cylinder about the open end thereof, and for controllably advancing said cylinder toward said body,
a pointed tube extending from the bore in said body at a distance from the open end of the bore in position to enter a container of liquid carried by said cylinder engaging said body and to supply liquid to said bore as said cylinder is advanced,
resilient means communicating with said bore at a distance from the open end thereof, and
means applying a force to said resilient means to store energy therein, and
means rapidly releasing said resilient means for applying a sudden pressure to liquid in said bore to eject the liquid therefrom.

5. An eye drop dispenser comprising,
a small open-ended tube adapted to contain an eye drop liquid to be dispensed,
aligning means engaging said tube for directing the open tube end toward an eye to be injected,
means defining a chamber for containing air,
piston means communicating with said chamber for compressing air therein, and
valve means connecting said chamber and said tube for suddenly applying compressed air from the chamber to the tube for forcibly ejecting said liquid from the tube end.

6. A liquid eye drop dispenser comprising
a thin elongated tube adapted to contain a predetermined amount of liquid,
pressure valving means connected to a first end of said tube, and
an injector compressing air and applying the compressed air to said pressure valving means for opening same at a predetermined pressure for rapidly applying the compressed air to the tube through said first end thereof for ejecting a fluid in the tube from a second end thereof.

7. The dispenser of claim 6 further defined by said injector including a movable plunger for compressing said air and said valving means comprising a spring loaded valve.

8. The dispenser of claim 6 further defined by said injector including means defining a chamber closed by said valving means, a heating coil disposed in communication with said chamber and controllable means controllably energizing said heating coil for compressing air in the chamber.

9. The dispenser of claim 6 further defined by a second heating coil adapted for disposition about said tube and connected to the means energizing said first heating coil for warming liquid in said tube prior to injection.

10. The dispenser of claim 6 further defined by
said injector comprising a housing defining a chamber therein and having a fine elongated opening extending from the bottom of the chamber to said tube, a hollow piston slidably disposed in said chamber above said opening and adapted to contain a liquid medicament, a hollow cylinder disposed axially in said piston with a small side opening and communicating with a very small opening in the bottom of said piston, a plunger extending through the top of said piston and having a shaft slidably disposed in said cylinder, and resilient means urging said piston upwardly in said chamber and said plunger upwardly from said piston.

11. Apparatus for injecting drops into the eye comprising
a housing having a small chamber therein and an opening through a wall thereof,
a plunger associated with said chamber for compressing air therein,
a mounting block movably mounted on said housing and adapted to releasably engage a thin elongated dispensing tube which in turn is adapted to contain an ophthalmic fluid,
said mounting block being controllably movable to place the rear end of said dispensing tube in communication with said housing opening,
means limiting the pressure of air compressed in said chamber for application to said tube to eject fluid from the front end thereof, and
aligning means for directing said tube into the eye at a short distance therefrom whereby fluid ejected from the tube is injected into the eye.

12. The apparatus of claim 11 further defined by said mounting block being pivotally mounted on said housing, and resilient means urging the block toward the housing with the rear end of the tube communicating with said housing opening.

13. The apparatus of claim 11 further defined by the means limiting the pressure of air comprising a thin membrane secured across the rear end of the dispensing tube which ruptures at a predetermined pressure.

14. The apparatus of claim 11 further defined by said dispensing tube having an internal volume of the order of 5 microliters per centimeter length.

* * * * *